US012165314B2

United States Patent
Lerch et al.

(10) Patent No.: US 12,165,314 B2
(45) Date of Patent: Dec. 10, 2024

(54) METHOD FOR GENERATING A TRAINED MACHINE LEARNING ALGORITHM

(71) Applicant: Siemens Healthcare GmbH, Erlangen (DE)

(72) Inventors: Daniel Lerch, Weilersbach (DE); Robert Tamas Derzsi, Wiesenttal (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 407 days.

(21) Appl. No.: 17/487,156

(22) Filed: Sep. 28, 2021

(65) Prior Publication Data
US 2022/0101526 A1 Mar. 31, 2022

(30) Foreign Application Priority Data
Sep. 30, 2020 (DE) ...................... 10 2020 212 315.2

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *G06F 18/214* (2023.01);
(Continued)

(58) Field of Classification Search
CPC ................ G06T 7/0012; G06T 11/008; G06T 2207/10081; G06T 2207/20081;
(Continued)

(56) References Cited

U.S. PATENT DOCUMENTS
2018/0350074 A1 12/2018 Schmidt

FOREIGN PATENT DOCUMENTS
EP 3409187 A1 12/2018

OTHER PUBLICATIONS

Rieke, N., Hancox, J., Li, W., Milletari, F., Roth, H. R., Albarqouni, S., Bakas, S., Galtier, M.N., Landman, B.A., Maier-Hein, K. and Ourselin, S., 2020. The future of digital health with federated learning. NPJ digital medicine, 3(1), p. 119.*
(Continued)

*Primary Examiner* — Zhitong Chen
(74) *Attorney, Agent, or Firm* — Harness, Dickey & Pierce, P.L.C.

(57) ABSTRACT

At least one embodiment relates to a method for training a machine learning algorithm. In an embodiment, the method includes provisioning a training apparatus with a machine learning algorithm to be trained, having a secure data connection to a medical-engineering imaging system; creating a plurality of training datasets based on image recordings, each training dataset of the plurality of training datasets being furnished with a ground truth or being linked by data link; sending training datasets, of the plurality of training datasets, to the training apparatus via the secure data connection; training the machine learning algorithm via the training apparatus, with the training datasets to create a trained machine learning algorithm; and sending a parameter dataset of the trained machine learning algorithm to the central computing apparatus via the data interface. A corresponding machine learning algorithm, a control facility, an imaging system and a multi-device network are also disclosed.

27 Claims, 3 Drawing Sheets

(51) Int. Cl.
*G06F 18/214* (2023.01)
*G06T 11/00* (2006.01)
*G16H 30/40* (2018.01)

(52) U.S. Cl.
CPC ............ *G06T 11/008* (2013.01); *G16H 30/40* (2018.01); *G06T 2207/10081* (2013.01); *G06T 2207/20081* (2013.01); *G06T 2207/20084* (2013.01)

(58) Field of Classification Search
CPC ..... G06T 2207/20084; G06T 2211/441; G06T 11/005; A61B 6/032; A61B 6/545; A61B 6/5217; G06F 18/214; G16H 30/40; G16H 40/40; G16H 50/20; G06N 3/126; G06N 3/08; G06V 2201/03; G06V 10/774
See application file for complete search history.

(56) References Cited

OTHER PUBLICATIONS

Xu, J., Glicksberg, B.S., Su, C., Walker, P., Bian, J. and Wang, F., 2019. Federated Learning for Healthcare Informatics. arXiv preprint arXiv:1911.06270.*

Kairouz, P., McMahan, H.B., Avent21, B., Bellet, A., Bennis19, M., Bhagoji13, A.N., Bonawitz, K., Charles, Z., Cormode23, G., Cummings, R. and D'Oliveira14, R.G., 2019. Advances and Open Problems in Federated Learning. arXiv preprint arXiv:1912.04977.*

Wang, F., Casalino, L.P. and Khullar, D., 2019. Deep learning in medicine—promise, progress, and challenges. JAMA internal medicine, 179(3), pp. 293-294.*

German Office Action mailed Jun. 15, 2021.

Xu et al., Federated Learning for Healthcare Informatics. (Aug. 20, 2020).

* cited by examiner

METHOD FOR GENERATING A TRAINED MACHINE LEARNING ALGORITHM

PRIORITY STATEMENT

The present application hereby claims priority under 35 U.S.C. § 119 to German patent application number DE 102020212315.2 filed Sep. 30, 2020, the entire contents of which are hereby incorporated herein by reference.

FIELD

Example embodiments of the invention generally relate to a method for generating a trained machine learning algorithm, in particular to a training method for the field of medical engineering.

BACKGROUND

Deep learning algorithms or machine learning algorithms (also referred to as "AI" for "Artificial Intelligence" below) are in widespread use in medical engineering. One frequent medical application consists in deriving a diagnosis from medical image data. Another application consists in applying AI to sensors which detect the shape and/or position of a patient in order to derive suitable parameters for recording images, e.g. for positioning or for data acquisition. In accordance with the prior art, an automatic isocentering of a computed tomography scanner ("CT scanner") is for example performed for this purpose via a 3D camera or automatic collimation for recording the anatomy of a patient in radiography.

AI algorithms require large volumes of data which represent a "ground truth" or "basic truth" to which the neural networks can be trained. In this case it must however be ensured firstly that these huge volumes of data are in compliance with the data protection regulations and secondly that they have to be annotated so that they comply with this ground truth. In the special case of training a neural network to determine ideal scanning or positioning parameters for recording images from signals from a sensor system this means that data which the sensors measure from patients and the imaging apparatus ideally should be provided together with the ground truth. This can be done e.g. by an operator who is supervising the training. The ground truth is typically the setting for scanning or position parameters that is or would be selected by a trained operator and is detected together with the sensor data.

For each training exercise, thousands or even tens of thousands of patient datasets are typically required for an AI to work in the desired range of accuracy of greater than 99%.

In order quickly to support a large quantity of AI-based tools to assist medical engineers in the parameter setting and positioning of imaging devices, it would ideally be desirable to gather large volumes of suitable sensor data quickly from each of the imaging devices present. Because of the costs and basic legal conditions this is very difficult, if not impossible, to implement in practice. The most serious problems are enumerated below.

i) The data packets that are collected and sent to a central hub for the training exercise are very large, in particular where images, sensor data or even live-streams are contained in the data, as is often the case. Transporting this data to a central data processing system and storing it there calls for significant technical effort and costs, in particular for legally compliant, safe storage.

ii) Legislation in many countries makes it difficult, if not impossible, to record or store data that can be used for the identification of a patient. In particular if the data is to be sent for further processing to a central data processing system of a provider. The consent of the patient is often required for this, which is only rarely given and considerably slows down the process of acquiring sufficient data for all the desired applications. Furthermore, additional costs are incurred for the additional effort.

SUMMARY

At least one embodiment of the present invention specifies an alternative, more convenient method and a corresponding apparatus for training a machine learning algorithm, with which at least one of the disadvantages described above can be improved upon or even prevented.

Embodiments are directed to a method, a machine learning algorithm, a control facility, an imaging system and a multi-device network.

An inventive method of at least one embodiment is used for training a machine learning algorithm or a machine learning unit (alternatively also called "AI" for short, see above), in particular of a deep-learning algorithm. The basic architecture of a machine learning algorithm is generally known and can be universally employed for a wide technical field. However, the question of which task the machine learning algorithm can solve and how well it can solve this task depends on the training. Thus in essence the training defines a specific machine learning algorithm.

If the internal structure of a machine learning unit or of a machine learning algorithm is examined, this AI comprises particular parameters, e.g. weighting parameters or the functional values of activation, propagation or output functions. The set of these parameters that are changed by a training process and that thus define the mode of operation of the trained AI are referred to as a "parameter set" below. They form the functional core of a trained AI. The values of the parameters of the parameter set are referred to as a "parameter dataset" below. An untrained AI (naturally with the same basic structure as the aforementioned AI), the parameter set of which is set in accordance with the parameter dataset, would work like the trained AI, since precisely those parameters that were also set during training now have the corresponding values.

The method of at least one embodiment comprises:
Provision of a training apparatus with a machine learning algorithm to be trained and with a secure data connection to a medical-engineering imaging system;
Provision of a central computing apparatus designed to operate a trained machine learning algorithm in a network without direct access to the secure data connection;
Provision of a data interface designed to send data from the training apparatus to the central computing apparatus;
Creation of a plurality of training datasets based on image recordings by the imaging system, which in each case are furnished with a ground truth or are linked by data link;
Sending the training datasets to the training apparatus via the secure data connection;
Training the machine learning algorithm via the training apparatus with the training datasets; and
Sending a parameter dataset of the trained machine learning algorithm to the central computing apparatus via the data interface.

An inventive system of at least one embodiment for training a machine learning algorithm comprises:
- a training apparatus with a machine learning algorithm to be trained, with a secure data connection to an imaging system,
- a central computing apparatus designed to operate a trained machine learning algorithm in a network without direct access to the secure data connection,
- a data interface designed to send data from the training apparatus to the central computing apparatus,
- a storage facility for a plurality of training datasets based on image recordings, which in each case are furnished with a ground truth or are linked by data link, and
- a communication unit designed to send training datasets to the training apparatus via the secure data connection (from the imaging system),
- wherein the training apparatus is designed to train the machine learning algorithm with the training datasets,
- and wherein the system is designed to send the parameter dataset of the trained machine learning algorithm to the central computing apparatus via the data interface.

An inventive machine learning unit of at least one embodiment, in particular an inventive machine learning algorithm of at least one embodiment, is preferably a CAD algorithm or an algorithm for positioning a patient in a medical-engineering imaging system and is trained in accordance with an inventive training method of at least one embodiment. This type of AI has the advantage that as a medical product it enables many steps in imaging to be automated and speeded up, and also permits error rates to be reduced. It can be used as a control element or as a computing module for the automated evaluation of data. As stated above, the training and thus the type of the training datasets determines the internal structure of the AI and thus its functionality. With direct training with patient data a suitable internal structure of the AI is achieved. With the inventive method of at least one embodiment, the independent use of the AI for a wide variety of systems is possible, without taking the safeguards for medical-engineering data into consideration and thus the simple and advantageous use of an AI that has been trained on one device on another device.

An inventive control facility of at least one embodiment is designed to control a (medical-engineering) imaging system, in particular a radiographic or tomographic system, and is configured for the performance of the method steps of an inventive method of at least one embodiment (performed in respect of the training therefore, e.g. in the hospital network). Alternatively or additionally, the control facility comprises the data interface and the training facility of an inventive system. The method steps relevant here are the ones that do not relate to the central computing apparatus, since this is located outside the hospital network.

An inventive (medical-engineering) imaging system of at least one embodiment, in particular a radiographic or tomographic system, comprises an inventive control facility. Preferred medical-engineering systems include X-ray devices and computed tomography systems as well as angiography devices (e.g. C-arm systems), magnetic resonance tomography systems, PET systems, SPECT systems or radiotherapy devices.

An inventive (medical-engineering) multi-device network of at least one embodiment comprises:
- a plurality of training apparatuses with secure data connections to different (medical-engineering) imaging systems (e.g. in secure hospital networks),
- a central computing apparatus designed to operate an inventively trained machine learning algorithm in a network without direct access to the secure data connections (e.g. outside the hospital networks),
- optionally further (medical-engineering) imaging systems, in particular in secure hospital networks or with the secure data connections that are configured to operate a trained AI (and that need not necessarily be designed for training an AI or for creating training datasets),
- data interfaces designed for data communication between the training apparatuses and the central computing apparatus, wherein the multi-device network is designed so that parameter datasets can be sent from the hospital networks to the central computing apparatus and vice versa.

A majority of the aforementioned components of the system or of a control facility can be implemented in a processor wholly or partly in the form of software modules. Implementation largely in the form of software has the advantage that even previously used control facilities can easily be retrofitted by a software update in order to work in the inventive manner. In this respect the object is also achieved by a corresponding computer program product with a computer program that can be loaded directly into a computer system or a storage facility, having program sections to execute all steps of at least one embodiment of the inventive method when the program is executed in the computer system. A computer program product such as this can if appropriate comprise, besides the computer program, additional elements such as e.g. documentation and/or additional components including hardware components, e.g. hardware keys (dongles, etc.) for the use of the software.

A computer-readable medium of at least one embodiment, e.g. a memory stick, a hard disk or another transportable or permanently installed data storage medium, can be used for the transportation to the computer system and/or for storage on or in the computer system on which the program sections of the computer program that can be read and executed by a computer system are stored. To this end the computer unit can e.g. have one or more cooperating microprocessors or the like.

A method of at least one embodiment for training a machine learning algorithm, comprises:
- provisioning a training apparatus with a machine learning algorithm to be trained, having a secure data connection to a medical-engineering imaging system;
- creating a plurality of training datasets based on image recordings, each training dataset of the plurality of training datasets being furnished with a ground truth or being linked by data link;
- sending training datasets, of the plurality of training datasets, to the training apparatus via the secure data connection;
- training the machine learning algorithm via the training apparatus, with the training datasets to create a trained machine learning algorithm; and
- sending a parameter dataset of the trained machine learning algorithm to the central computing apparatus via the data interface.

At least one embodiment is directed to a machine learning algorithm stored on a non-transitory computer readable medium, trained in accordance with the method of an embodiment.

At least one embodiment is directed to a control facility for controlling an imaging system, configured to train a machine learning algorithm by at least:

provisioning a training apparatus with a machine learning algorithm to be trained, having a secure data connection to a medical-engineering imaging system;

creating a plurality of training datasets based on image recordings, each training dataset of the plurality of training datasets being furnished with a ground truth or being linked by data link;

sending training datasets, of the plurality of training datasets, to the training apparatus via the secure data connection;

training the machine learning algorithm via the training apparatus, with the training datasets to create a trained machine learning algorithm; and sending a parameter dataset of the trained machine learning algorithm to a central computing apparatus via a data interface.

At least one embodiment is directed to an imaging system comprising a control facility an embodiment.

At least one embodiment is directed to a multi-device network comprising:

a plurality of training apparatuses with secure data connections to different imaging systems;

a central computing apparatus designed to operate the trained machine learning algorithm of claim 10 in a network, without direct access to the secure data; and data interfaces designed for data communication between the plurality of training apparatuses and the central computing apparatus, wherein the multi-device network is designed to enable parameter datasets to be sent to and from the plurality of training apparatuses to the central computing apparatus.

At least one embodiment is directed to a non-transitory computer program product storing a computer program, directly loadable into a computing facility, including program sections to execute the method of an embodiment when the computer program is executed in the computing facility.

At least one embodiment is directed to a non-transitory computer-readable medium, storing program sections, readable and executable by a computer unit, to execute the method of an embodiment when the program sections are executed by the computer unit.

BRIEF DESCRIPTION OF THE DRAWINGS

The invention is explained once again below in detail with reference to the enclosed figures using example embodiments. The same components are provided with identical reference characters in the various figures. The figures are generally not to scale, and show.

DETAILED DESCRIPTION OF THE EXAMPLE EMBODIMENTS

Figure 1:
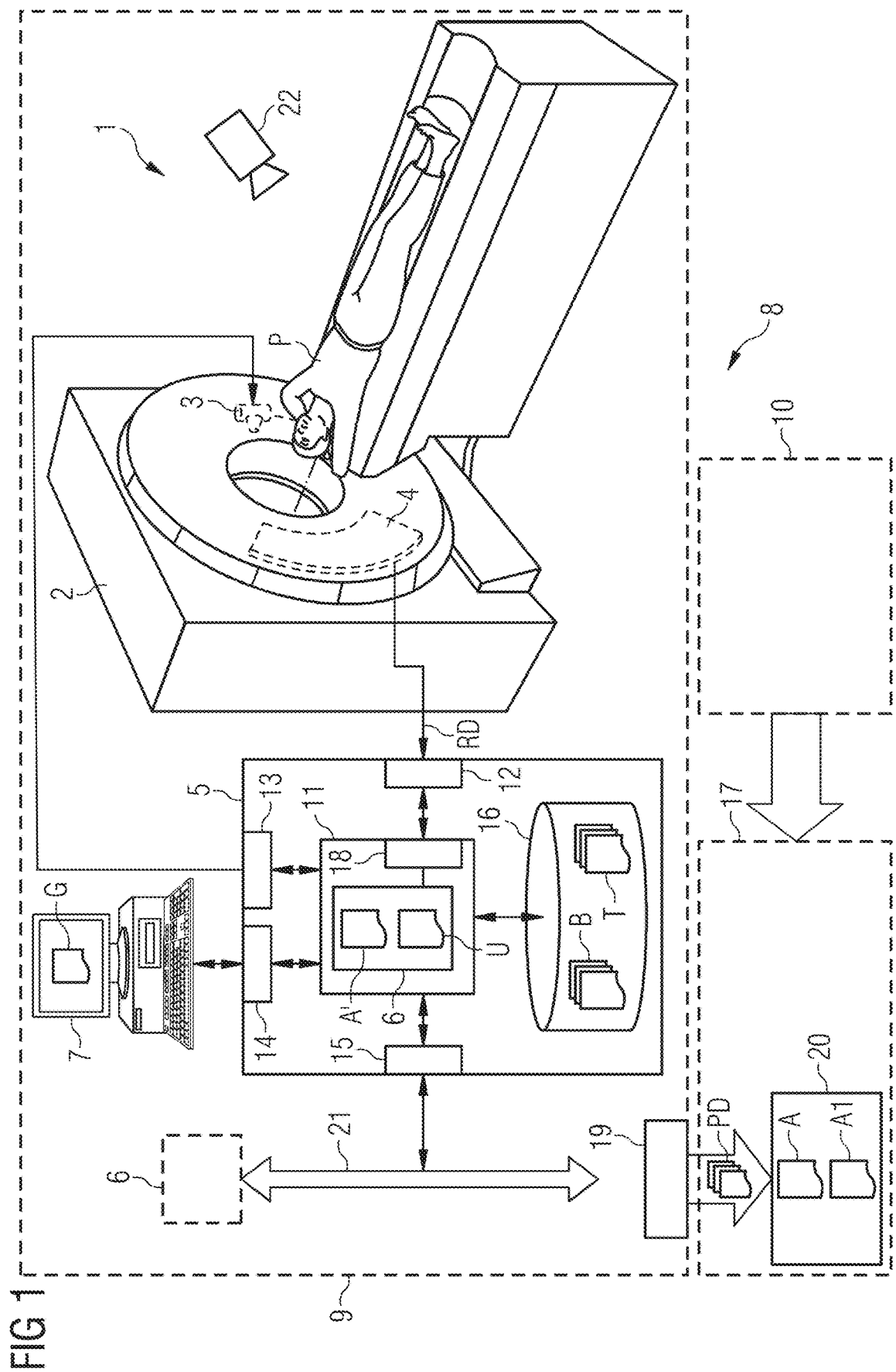
FIG. 1 a roughly schematic representation of a computed tomography system with an example embodiment of the inventive apparatus for the performance of the method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method of at least one embodiment comprises:
Provision of a training apparatus with a machine learning algorithm to be trained and with a secure data connection to a medical-engineering imaging system (e.g. within a secure hospital network).

The training apparatus in this case is a computer system which is designed to train a machine learning algorithm, and the basic structure of which is well known in the prior art. The training apparatus is preferably accommodated in a medical imaging system, e.g. in the control facility thereof, or in a computing facility outside the imaging system.

The data connection can be implemented via a network, or else via a cable connection or a data bus. Examples of this would be a WLAN, a LAN or simply a data connection via USB. For example, one or more devices in a hospital can be in data contact with the training apparatus via a hospital network. However, in just the same way, a device in a doctor's practice can also be connected to a training apparatus via data cable, or in the case of a patient at home a "point-of-care" medical device can contain a training apparatus which receives its training data directly via a data bus.

It is important that this data connection is secure, so that no one has unauthorized access to the data. An example of this is a secure hospital network as well as the data cable or a data bus.

In particular a secure data connection in the form of a hospital network is known to the person skilled in the art. This is a network which is used by a hospital to send patient-specific information internally. For example, the hospital network is the network of an RIS (Radiology Information System) or PACS (Picture Archiving and Communication System). This type of hospital network is secure as standard, e.g. via firewalls or via specially secured contact points to other networks. In this type of network the basic legal conditions for sending and processing patient data are satisfied by these appropriate security measures and the provision and storage of data for the purpose of training an AI are also generally not subject to any additional regulatory or legal hurdles other than the rules already satisfied in any case within the network.

Provision of a central computing apparatus designed to operate a trained machine learning algorithm in a network without direct access to the secure data connection (e.g. outside the hospital network).

This central computing apparatus is e.g. a server or an otherwise high-performance computer system and lies outside the safeguards of the data connection (e.g. of the hospital network). This does not necessarily mean that this computing apparatus must also always be outside of a hospital. The crucial point here is the boundary of the network to the data connection. The data connection is designed so that sensitive patient data in it can be sent in accordance with the prevailing legal requirements; these restrictions do not necessarily apply for the other network (e.g. public parts of the Internet). The term "direct" means that an indirect access by the other network to the secure data connection via the data interface described below may perhaps be possible (but then only via specially secured access facilities, so that no sensitive data can fall into the hands of unauthorized persons). However, it is preferable for the other network to have no access at all to the secure data connection and for the data interface to only permit communication between training apparatus and central computing apparatus.

Provision of a data interface designed to send data from the training apparatus to the central computing apparatus.

Data can thereby thus be sent from the training apparatus to the computing apparatus via the other network. Since the training does not take place in the computing facility, this need not however be sensitive patient data.

The data interface is preferably designed for data communication between training apparatus and central computing apparatus, so that the training apparatus can also receive data from the central computing apparatus, e.g. an AI trained elsewhere. The important thing here is that the data interface to the central computing facility or the other network should not permit any access to sensitive data. The data interface is therefore designed to protect the security of the data connection to the medical-engineering imaging system.

Creation of a plurality of training datasets based on image recordings by the imaging system (therefore e.g. within the hospital network), which in each case are furnished with a ground truth or are linked by data link.

These training datasets generally contain sensitive data, e.g. patient data. The training datasets preferably comprise a plurality of image recordings or data for recording the image recordings, e.g. positioning data or data for presetting a recording device. One image recording (2D or 3D, photos or X-rays) should at least have been taken for each training dataset and data from this or data derived therefrom or data that resulted in the recording thereof should have been included in the respective training dataset. The data preferably relates to a (medical-engineering) imaging system or image recordings thereof. It should be noted here that the recording of training datasets is carried out in the place (e.g. in the same hospital network) into which the training apparatus is also integrated. Hence sensitive data need not be sent via insecure connections, but only within the secure data connection.

The ground truth broadly speaking comprises everything that the AI predefines for how a problem should be solved correctly. Data which is of the type that the AI is to process subsequently then forms part of the training dataset but in particular not of the ground truth. For example, examination-specific data (type of examination, patient data or images for CAD) forms part of the training data (but in particular not of the ground truth). In contrast, details of physicians or an additional AI for correcting a statement or setting preferably form part of the ground truth. In contrast, settings may form part of the ground truth if they resulted in correct images (since then e.g. the position or collimation was correct) but not necessarily if corrections were needed (these corrections would then be part of the ground truth). As regards sensor data on which these settings of the ground truth were based, it should preferably be counted as training data forming part of the ground truth.

Thus examination-specific data which represents the type of the examination, or details of a patient, such as e.g. height, sex, weight of the patient, is typically training data, e.g. for a desired automatic positioning or presetting of an imaging system. For a CAD algorithm, image recordings should be contained in the training data. For the problem of device positioning/setting or collimation, sensor data of the patient should also be used as input parameters, in other words as training data.

However, depending on the application, sensor data can also be part of the ground truth. For example, if the correct positioning of the patient is to be evaluated by the AI in order to indicate to the user that e.g. the elbow should be angled further forward, it would be advantageous to assign the sensor data to the ground truth. It is also advantageous for an avatar or a digital patient model (e.g. from a skeletal recognition or using a grid) of the patient to be created based upon the sensor data and for this to be regarded as ground truth for the problem of patient positioning. Sensor data or avatars created based upon sensor data (which in particular includes digital models, skeletal models, point clouds or grids of the patient) can generally, for the problem of correct patient positioning to be modeled by an AI, form part of both the training data and the ground truth, if it resulted in correct images or treatments, since the patient positioning was then correct. If corrections were needed, this data must be correctly sorted accordingly. The anatomical data of the patient determined from sensor data (e.g. length of lower arm, thigh, width of the hip, abdominal girth, etc.) is then preferably contained in the training dataset and the final positioning of the patient (angles of all joints and their position relative to the geometric degrees of freedom of the medical device) is contained in the ground truth.

It is in particular preferred for a further image analysis to be integrated into the method, in which the quality of image recordings is assessed and the result thereof is included in the corresponding training datasets as ground truth.

The training data need not necessarily originate from one single device. It can also originate from multiple devices, providing these are all connected to the training apparatus via a secure data connection (e.g. they are all located in the same hospital network). The trained AI networks collected in the central computing apparatus (central hub) can then in turn originate from multiple different protected hospital networks.

Sending the training datasets to the training apparatus via the secure data connection (e.g. within the hospital network).

This is possible as indicated above, because the imaging system is connected to the training apparatus via this secure data connection.

Training the machine learning algorithm via the training apparatus with the training datasets.

The procedure for training a machine learning algorithm is known to the person skilled in the art and comprises processing the training datasets in the light of the ground truth.

Sending a parameter dataset of the trained machine learning algorithm to the central computing apparatus via the data interface.

Since the training of the AI does not take place on the central computer (outside a secure environment), but inside, but other locations should also access the trained AI, and the AI can if necessary be further improved in retrospect, as is explained in greater detail below, the data for the trained AI should be passed to the central computing apparatus. This is achieved by sending the parameter dataset, without unauthorized persons receiving sensitive patient data, since this can no longer be extracted from the parameter dataset.

One advantage of at least one embodiment of the inventive method is that complete training datasets can be used for training an AI despite regulations and safeguards of medical data connections for training an AI and the trained AI can nevertheless be used outside the safeguards. For example, 2D/3D sensor data and (complete) clinical input parameters can be used for the training, together with radiological (X-ray/CT/MR) images, even if the trained AI is used subsequently by completely different institutions. Even public use would be possible, without sensitive data being disclosed. Furthermore, it is possible to collect different trained AIs from different institutions. With this method it is therefore possible, when compiling training data and ground truth, to access all necessary data, because all of it is present in situ (e.g. in a clinic). Another advantage is that the local training enables the ground truth to be adapted to "local preferences" or patient cohorts. This increases customer acceptance and thus the value of the algorithms. The AI thus no longer suggests an across-the-board mean as a solution for problems, but learns in line with the wishes and practices of a specific clinic.

The consistent application of this method to all problems that can be supplied to an automation system by sensors generally results in increased standardization in imaging methods and thus avoidance of errors and a reduction in time spent on diagnostics.

An inventive system of at least one embodiment for training a machine learning algorithm comprises:
  a training apparatus with a machine learning algorithm to be trained, with a secure data connection to an imaging system,
  a central computing apparatus designed to operate a trained machine learning algorithm in a network without direct access to the secure data connection,
  a data interface designed to send data from the training apparatus to the central computing apparatus,
  a storage facility for a plurality of training datasets based on image recordings, which in each case are furnished with a ground truth or are linked by data link, and
  a communication unit designed to send training datasets to the training apparatus via the secure data connection (from the imaging system),
  wherein the training apparatus is designed to train the machine learning algorithm with the training datasets,
  and wherein the system is designed to send the parameter dataset of the trained machine learning algorithm to the central computing apparatus via the data interface.

An inventive machine learning unit of at least one embodiment, in particular an inventive machine learning algorithm of at least one embodiment, is preferably a CAD algorithm or an algorithm for positioning a patient in a medical-engineering imaging system and is trained in accordance with an inventive training method of at least one embodiment. This type of AI has the advantage that as a medical product it enables many steps in imaging to be automated and speeded up, and also permits error rates to be reduced. It can be used as a control element or as a computing module for the automated evaluation of data. As stated above, the training and thus the type of the training datasets determines the internal structure of the AI and thus its functionality. With direct training with patient data a suitable internal structure of the AI is achieved. With the inventive method of at least one embodiment, the independent use of the AI for a wide variety of systems is possible, without taking the safeguards for medical-engineering data into consideration and thus the simple and advantageous use of an AI that has been trained on one device on another device.

An inventive control facility of at least one embodiment is designed to control a (medical-engineering) imaging system, in particular a radiographic or tomographic system, and is configured for the performance of the method steps of an inventive method of at least one embodiment (performed in respect of the training therefore, e.g. in the hospital network). Alternatively or additionally, the control facility comprises the data interface and the training facility of an inventive system. The method steps relevant here are the ones that do not relate to the central computing apparatus, since this is located outside the hospital network.

An inventive (medical-engineering) imaging system of at least one embodiment, in particular a radiographic or tomographic system, comprises an inventive control facility. Preferred medical-engineering systems include X-ray devices and computed tomography systems as well as angiography devices (e.g. C-arm systems), magnetic resonance tomography systems, PET systems, SPECT systems or radiotherapy devices.

An inventive (medical-engineering) multi-device network of at least one embodiment comprises:
  a plurality of training apparatuses with secure data connections to different (medical-engineering) imaging systems (e.g. in secure hospital networks), a central computing apparatus designed to operate an inventively trained machine learning algorithm in a network without direct access to the secure data connections (e.g. outside the hospital networks), optionally further (medical-engineering) imaging systems, in particular in secure hospital networks or with the secure data connections that are configured to operate a trained AI (and that need not necessarily be designed for training an AI or for creating training datasets), data interfaces designed for data communication between the training apparatuses and the central computing apparatus, wherein the multi-device network is designed so that parameter datasets can be sent from the hospital networks to the central computing apparatus and vice versa.

A parameter dataset is therefore sent to the central computing apparatus by a training unit, if appropriate in a (medical-engineering) imaging system, via one of the data interfaces which connect the individual users to the central computing apparatus. It must be remembered that it is not ruled out that other parts of the trained AI (thus also the entire trained AI) can also be sent, it however being preferable not to send the entire AI (in other words not to send parts of the basic architecture of the machine learning algorithm). It is preferable for the system additionally to be configured such that the central computing apparatus can also send parameter datasets back to the (medical-engineering) imaging systems. The advantage of this is that a trained AI that was trained on an imaging system with sensitive patient data can be sent via the central computing apparatus (where if appropriate it was evaluated or combined with another AI) to a different or to the same medical-engineering imaging system. To this end the central computing apparatus is preferably designed to combine parameter datasets or machine learning algorithms with one another and in particular to create a resulting parameter dataset via at least two parameter datasets.

It should be noted that the parameter datasets sent by the training apparatus to the central processing unit have a high economic value. Simply because the network in question need not be secured in the same way as the data connection between imaging system and training apparatus, this does not mean that the parameter datasets should be sent via an unsecure connection. It is merely the case that the same safeguards do not need to be present in the network as for the data connection. It is therefore an advantage if the transmission of the parameter dataset takes place in a secure and/or encrypted manner. In a network with multiple (training) users with a central unit a transmission could in particular also be based on blockchain technology.

Even though embodiments of the invention are especially advantageous for the medical field, e.g. for training an algorithm to support the diagnosis of clinical pictures, other applications can also be advantageously improved by the invention. The method can in principle be used whenever the training datasets contain sensitive data. The imaging systems need not then necessarily be of a medical-engineering nature.

It is once again stressed at this point that the training takes place in a hospital network, in other words so to speak "in situ". This means that the sensitive (patient) data may in fact leave the imaging system ("modality"), but not the hospital network per se. The boundary in this case is therefore outside the IT of the hospital (but not necessarily the spatial boundary of the hospital). The training can just as well take place on the modality as on another computer in the hospital IT, depending on where the training apparatus is accommodated. For regulatory reasons it may even make more sense for the application to be outside the modality on a separate computer (e.g. in the same hospital network). The fact of passing beyond spatial boundaries is irrelevant for most applications in terms of data security and thus for the method. If the method is applied in a group of hospitals consisting of multiple hospitals, "in situ" can also mean "in one of the hospitals in the group", providing these hospitals are connected to one another by a single hospital network. It is thus possible to transfer the training datasets between all hospitals in the group across the physical boundaries of the hospitals (but within the hospital IT). The central computing facility can then be located with the manufacturer of the modalities and can contain AI trained by many other hospitals, with which it can later also support the group with better trained AI.

In practice a network, in particular the hospital network, can comprise a LAN or WLAN. A common instance of a hospital network is a branched network for university institutions or a private hospital branch system. Even in the case of branched hospital networks the training datasets always remain within the secure hospital network and are not sent outside to the manufacturer of the medical devices or into a cloud (only parameter datasets).

A majority of the aforementioned components of the system or of a control facility can be implemented in a processor wholly or partly in the form of software modules. Implementation largely in the form of software has the advantage that even previously used control facilities can easily be retrofitted by a software update in order to work in the inventive manner. In this respect the object is also achieved by a corresponding computer program product with a computer program that can be loaded directly into a computer system or a storage facility, having program sections to execute all steps of at least one embodiment of the inventive method when the program is executed in the computer system. A computer program product such as this can if appropriate comprise, besides the computer program, additional elements such as e.g. documentation and/or additional components including hardware components, e.g. hardware keys (dongles, etc.) for the use of the software.

A computer-readable medium, e.g. a memory stick, a hard disk or another transportable or permanently installed data storage medium, can be used for the transportation to the computer system and/or for storage on or in the computer system on which the program sections of the computer program that can be read and executed by a computer system are stored. To this end the computer unit can e.g. have one or more cooperating microprocessors or the like.

Further particularly advantageous embodiments and developments of the invention emerge from the claims and the following description, wherein the claims in one claim category can also be developed analogously to the claims and parts of descriptions to form another claim category and in particular individual features of different example embodiments or variants can be combined to form new example embodiments or variants.

As regards the contents of the training datasets or the ground truth, this very largely depends on the problem which the AI is subsequently to solve.

For example, the setting of an operator applied to a particular patient can be part of the training datasets. Data from a sensor can then be regarded as ground truth (but see the explanations above). A further example of an approach consists in letting the operator assess the selection of the parameters retrospectively, after the images have been recorded (and their suitability can be examined), which would be incorporated into the ground truth. Depending on the operator's assessment, the operator's own work results can be used to weight the datasets in the training datasets. It is in particular preferable for a radiologist to assess the quality of the image result (e.g. the extent of its collimation or the isocentering) and then to give his/her assessment of a further optimized setting, which is then transferred to the training dataset.

The suitability of a dataset for the ground truth could preferably be determined in three different versions with increasing precision:

a) After an image recording an MTRA or another user personally assesses based upon the recording whether the recording was good (noise behavior, angle or distance of the X-ray source, kV, mAs of the X-ray source) and assesses the result as good or bad. The assessment often takes place implicitly, in that the result is forwarded for the diagnosis or is deleted and a new recording is made.

b) After an image recording a secondary AI assesses whether the aforementioned parameters have resulted in a good image and confirms the result as good or signals to the user that it should be rejected. In some cases (such as e.g. the collimation of an X-ray or tomography recording) the secondary AI can also itself adjust or improve the result (e.g. by trimming or cropping the resulting radiological images). The user can then once again make a final decision about this. The finally confirmed result is then incorporated into the ground truth.

c) Once a secondary AI and/or MTRA/user has already confirmed that the image is good and has forwarded it, a radiologist appraises the image (see above: this is preferably incorporated into the ground truth) as successful or rejects the image as diagnostically unacceptable and requests a new examination or carries out a limited diagnosis, but sends negative feedback about the image, e.g. to an RIS or PACS system.

Further developing at least one embodiment of the inventive method through the use of a secondary AI to create or supplement a ground truth additionally solves the problem that "manually" created training datasets often lack important details in the ground truth, because such datasets are almost always incomplete. However, a manual annotation is also complex, expensive and sometimes defective. Because this method permits a ground truth to be determined automatically, the creation of training datasets becomes very inexpensive. As soon as the acquisition of training data and ground truth is no longer limited by high costs, training data can be provided simply and economically, which speeds up the training of an AI considerably and also increases its quality and thus its value.

The dataset of a ground truth can then comprise one or more of the following data types depending on the modality, e.g. for the problem of positioning:

a) The ideal position of an imaging device (detector, X-ray tube, collimator, table height, coil positions, collimator positions, etc.), b) the parameters of the image recording (kV, mAs, MR sequence or gradient strength, etc.), c) the position of the patient relative to the modality (or to individual components of the modality) or the angular position of joints.

d) the position of a medical implant identified in a medical image relative to anatomical structures of a patient identified thereon or correlated based upon sensor data. This applies in particular to medical images created in situ in the context of therapeutic applications such as surgery, angiography or radiotherapy.

The ground truth in the case of a CAD application is preferably a clinical diagnosis and the marking or delimitation thereof on a clinical image (X-ray, CT, MR, SPECT, PET).

The ground truth can be predefined by a medically trained user, e.g. an MTRA, a medical assistant with X-ray certification or a physician. However, it can also be created automatically by a secondary AI, e.g. by the results of a cropping algorithm. A medically trained user optionally confirms the result of an automatically created ground truth.

According to a preferred method the quality of the image recordings is analyzed based upon predefined criteria before the training datasets are sent to the training apparatus. If the quality does not satisfy the predefined criteria, the image recording is adjusted so that it corresponds to the criteria or it is rejected. The analysis can be performed by a user, but also automatically, e.g. by a specially trained AI. The image recording need not necessarily be part of a training dataset, even if this is a preferred case. For example, the training dataset can comprise data for positioning a patient for recording a predetermined body region and the image recording is used to check whether or not this data has resulted in a good recording.

Possible criteria are known to the person skilled in the art and correspond to those criteria in accordance with which the person skilled in the art personally appraises the image recordings. Possible criteria are:

the size of the sectional image (can the subject be seen in the right size or is it too small or too big?)

the position of the sectional image (is the subject shown in the correct position, e.g. in the center?)

the signal-to-noise ratio (is the image too noisy?)

the correct subject (is the right object or organ shown?)

the correct representation (for example, has the joint space been transirradiated at the right angle so that it is readily visible?)

The presence of artifacts (e.g. a kinetic blurring or artifacts caused by metals).

It is in this case preferable that if the image recording has been adjusted, it is included in the respective ground truth. Thus if e.g. cropping has occurred (part of the image recording has been cut off), because the size of the sectional image was selected incorrectly (e.g. by collimation) during the recording, this is included in the ground truth and e.g. data for setting a collimator is thereby provided with a "label".

For example, a 3D camera or another sensor monitors this process while a patient is being scanned with a particular collimation (besides other imaging parameters) that is specified by the user or suggested by the previously trained AI algorithm. An image analysis algorithm that acts on the detected medical image then segments the image in order to identify a predetermined organ (e.g. the lungs for a thorax p.a. radiography examination). Such algorithms are already known today and are generally referred to as "automatic cropping algorithms" (or just "cropping algorithms"). The ground truth for the local training of the neural network then preferably comprises the resulting ideal size of the medical image, i.e. the result of the automatic cropping algorithm. In a similar manner an analysis of the medical image can be used also to evaluate the selection of tube voltage and tube current, in order to determine a ground truth for other imaging parameters. For this purpose the approach should be combined with algorithms, which e.g. evaluate the signal-to-noise ratio of the image recording and from this can deduce which recording parameters were incorrect and if appropriate determine correct values (in particular kV and mAs in the case of an X-ray-based recording). Likewise an algorithm can in particular calculate for a tomographic examination whether for the previously selected position of the patient in the gantry of the medical device the center of the body or its radiological center of gravity actually correlated with the isocenter of the gantry. Should there be deviations, this can be taken into consideration in the ground truth.

In the event that an image recording cannot be adjusted such that it corresponds to the criteria or that it was rejected (by a user or another AI), the corresponding training dataset is preferably rejected or is characterized as a negative example.

It is often the case that neither an automatic image analysis algorithm for cropping or adjusting an image nor the input by an operator results in the ideal image quality desired by the radiologist reading it. Regardless of the skills of the operator or the quality of the algorithm, this is always the case up to a certain point, since the preference for the representation of images is up to a certain point a question of the personal taste of the physician doing the reading. It is therefore preferred for the opinion of the physician doing the reading also to be incorporated into the ground truth. Preferably the physician can insert a marker for the appraised images as ground truth into the corresponding training datasets via a software interface, e.g. a "(not) correct" for presettings or results of a preliminary image evaluation.

This feedback (and preferably therefore also the ground truth) can optionally contain additional information, e.g. how adequate the settings for cropping, tube voltage or tube current were. The feedback can however also contain the information that the physician has regarded the image quality as inadequate. The information from the physician that results in an image quality suitable for reading is preferably to be regarded as ground truth.

The advantage of this additional human-machine interface consists in a minimization of the probability of the AI being trained to a suboptimal ground truth that was falsified either by a suboptimal image analysis algorithm or by inadequately qualified operators. In addition, this would result in a more selective training of the machine learning algorithm in the direction of a standardized image quality, as is desired by the local physicians in the respective facility. Comprehensive training with feedback from diagnosticians could also have the advantage that the standardization of the perception of the image can be achieved across the board, since even radiologists in a single institution are often not in agreement as to which ideal perception of the image should be regarded as standard. If the information in question is included in the training that the physician doing the reading has marked, the AI algorithm could even be trained to adjust the image recording settings depending on who the referring physician or the radiologist doing the reading is.

In respect of the ground truth, different variants of the imaging of the ground truth come into consideration, depending on which parameter of the imaging examination of the AI to be automated or to be learned is to be trained.

In the case of an image recording, the position of a patient can be measured in advance, e.g. via a 3D sensor such as a 3D camera. The position of this can be part of the training dataset and a confirmation of this position or of the image recording (for a correct image recording) or the corrected position (for a corrected image recording) is preferably included in the ground truth. However, it can also be the case that after a user has positioned a patient, the AI trained previously in accordance with the method establishes that the positioning deviates from the ideal (and if appropriate it warns the user). For the resulting image recording the user can now mark whether or not the user's selected position has generated a good image recording. This marking is then preferably also part of the ground truth. The image recording itself need not be part of the training dataset.

However, the tube voltage and/or the tube current can also be set. Once an image recording has been produced an algorithm measures the noise behavior of the image recording and calculates whether contrast and noise are as desired in the image recordings or whether the recording was made using a dose that was too high or too low. The training dataset then comprises data on the original setting of the tube voltage or tube current. The ground truth preferably comprises a confirmation that the image recording was or was not good, or the better data on this suggested by an algorithm. Here too, the image recording itself need not be part of the training dataset.

For example, in the field of radiography or in standard X-raying a collimation can be set by a user. If the image recording is accepted by the user without manual cropping in the generated X-ray image, the training dataset or the ground truth (depending on the problem) preferably comprises the collimator setting. It is particularly preferred for the ground truth to comprise information that the image recording was good (and if appropriate 3D sensor data). For example, in the case of an AI-controlled collimation the training dataset contains the clinical objective or request and if appropriate the data from a 3D sensor and the ground truth contains the collimation selected for a respectively generated image, in particular if the result was accepted without retrospective cropping.

A collimation can however also be set by a previously trained AI (based upon the data from the 3D sensor). The cropping can likewise be performed by a further trained AI. If e.g. the cropping of the image is readjusted by the user or the AI, the ground truth should additionally also comprise the modification of the collimation based upon the cropping (of the AI or of the user).

It may however (additionally) be the case that the angle between the detector and the object has been set, e.g. a pretrained algorithm (a rejection analysis algorithm) or a user sets the angle of an X-ray tube to the knee. If the angle is correct it should also (depending on the problem) be included in the training dataset or the ground truth, and in the ground truth additionally the information that the image recording was good. For example, if in the case of an AI-controlled setting of the angle the training dataset contains the clinical objective or request and if appropriate the data from a 3D sensor and the ground truth contains information about the correct angle. If the user or an additional trained AI recognizes in the image recording that the angle was incorrect, e.g. that the knee joint space cannot be identified, the image recording may be rejected or characterized as a negative example. Alternatively however it may also be determined at what angle the recording should have taken place and this determined angle is then preferably incorporated into the ground truth. Thus an AI can be trained to complex positioning parameters such as e.g. the angle between X-ray tube, detector and organ of interest.

It can however also preferably be determined by a user or a trained AI whether the image recording relates to a right-side or left-side image of the patient and the corresponding side, e.g. a label "L" or "R", is then added to the ground truth.

In the case of a tomographic recording (CT, SPECT, PET, etc.), the height of the CT table can be set to the calculated ideal isocenter by a user following a measurement of the patient or the latter's position. After a CT scan a user or a further trained AI calculates the radiological "center of gravity" of the body from the images and thus the ideal isocenter. The information required for this (a marker that marks a "good recording", or a determined ideal isocenter) is then preferably part of the ground truth and position data of the patient or the isocenter set is preferably part of the training dataset.

An optimal isocentering for a CT examination can however also be calculated or predicted via an AI, and is based on the detection of the position of the patient by suitable sensors such as 3D cameras, ultrasound or radar sensors. After a CT image recording the resulting image volume is analyzed to find out where (on the local average) the correct isocentering for the scanned body volume would have taken place (see above). The result is then preferably used as ground truth in combination with the detected 3D camera data.

In accordance with a preferred method the analysis of the image recordings, exclusively or in addition to an analysis by a user, is performed via a previously trained verification algorithm which evaluates the quality of a respective image recording based on the predetermined criteria. If the respective image recording does not satisfy the predetermined criteria, the AI preferably also ensures that the image recording is adjusted, such that it corresponds to the criteria, and/or it determines which recording parameters had to be changed during the recording, and how, so that the image recording would satisfy the criteria. In this case it is preferably determined based upon the adjusted image recording, how during the original image recording the positioning of the patient, in particular a positioning and/or an isocentering, should have been effected so that it would have satisfied the criteria.

The additional AI preferably analyzes a medical-engineering image recording (e.g. a radiological image) for relevant organs in the image (AI such as this is the prior art) and decides whether the settings made previously for the examination were good, e.g. whether all organs are contained at the correct angle and in full. The results of the analysis are then preferably transferred into the ground truth.

In accordance with a preferred method the ground truth assigned to an image recording comprises (in particular exclusively) information about which settings have been made for recording the respective image recording and/or which changes to the image recording have been made. Possible settings would be e.g. of a collimation or positioning of a patient, possible changes would be e.g. corrections, in particular a retrospective cropping of the image recording. In this case the information is preferably automatically recorded when making the respective settings. In this case examination-specific details on the nature of the examination and if appropriate patient data are preferably part of the training dataset.

The AI is therefore preferably trained (in particular only) based upon the image setting behavior (e.g. of the collimation) monitored by the user and any corrections that may have been made (e.g. the manual corrections by the user during retrospective cropping of the image), and thus learns its "behavior" purely from the user's behavior. In addition, the training datasets preferably also contain information about whether or not the image recording was found to be good. Together with the information about the settings an advantageous training can be carried out, in which the quality of the settings is taken into consideration.

However, another preferred case is one in which a radiologist appraises a radiological image, on which clinical pictures identified by a correspondingly trained AI are additionally displayed to the radiologist. The radiologist confirms the correct clinical pictures or marks the incorrect clinical pictures or adds clinical pictures which the AI has not identified. These image recordings can also be included in the training datasets and the opinion of the radiologist can be included in the ground truth. The AI to be trained would then preferably be a CAD ("Computer Aided Diagnosis") algorithm.

In accordance with a preferred method the machine learning algorithm is a CAD algorithm and the ground truth for an image recording comprises a diagnosis and preferably in addition information on a postprocessing of the image recording, in particular information on changes of contrast, brightness, highlighting of structures or changes to the positions of picture elements.

A preferred method is designed, in particular in respect of the selection of the machine learning algorithm and the training datasets, to train the AI to specify the parameters for a radiological examination on a patient-specific basis, in particular parameters of the degrees of freedom of the modality and/or of the position of the patient, preferably parameters of the group consisting of collimation, dimensioning of spatial axes, orientation of a coordinate system, tube voltage ("kV"), X-ray current, intensity of the X-ray beam (e.g. mAs), position of the patient or of a patient couch, orientation of the patient or of a patient couch, position of a recording window and recording time. This is achieved by including the corresponding parameters in the training datasets.

In accordance with a preferred method, sensor data is recorded by the corresponding medical-engineering imaging system or a sensor connected thereto in the context of the creation of training datasets in addition to the image recordings (i.e. in advance of, during or after the recording, but directly relating to this recording). This sensor data is in particular position data on the position of a patient.

The sensor data in particular comprises image data from a camera, preferably data from a 3D camera and/or data from an ultrasound detector and/or data from a radar detector. Pure RGB camera data can however also be used.

In accordance with a preferred method at least two trained machine learning algorithms or parameter datasets thereof are used for mutual evaluation and/or validation in the central computing apparatus.

Machine learning algorithms are preferably used that have been trained on identical objects, in particular organs. This should be such that an effective evaluation or validation can take place. It is preferred in this case for a number of the machine learning algorithms used for this purpose to have been trained within secure environments (via secure data connections in each case, e.g. in different hospital networks). Particularly preferably in this case, the best evaluated and/or validated machine learning algorithm is made available by the central computing apparatus for use by medical facilities. The advantage of this is that every AI can regularly be improved by other trained AIs and the respectively best trained AI can be used.

In accordance with a preferred method at least two trained AIs or parameter datasets thereof are combined and/or mixed with one another in the central computing apparatus.

Thus the training can take place at multiple locations (in multiple clinics) in parallel and can be further processed or mixed in the central computing apparatus. Machine learning algorithms are preferably used that have been trained on identical objects, in particular organs. This should be such that an effective evaluation or validation can take place. It is preferred in this case for a number of the machine learning algorithms used for this purpose to have been trained within secure environments (via secure data connections in each case, e.g. in different hospital networks). Particularly preferably in this case, a machine learning algorithm resulting from the combination and/or mixing is made available by the central computing apparatus for use by medical facilities.

For example, in the context of an automatic thorax identification the technique for thorax identification, collimation and the voltage setting for the X-ray tube are taken over by an AI that has been trained at a facility with multiple thorax examinations, and the technique for an identification of shoulders (or corresponding settings of the device) is taken over by an AI that has been trained in a facility which specializes in the examination of shoulders.

A combination or mixture can in particular be performed via complex mixing diagrams, in particular with the aid of meta-algorithms such as e.g. "genetic algorithms", which then leads to a resulting meta-AI. This meta-AI combines the strengths of the combined or mixed AI for an optimal clinical deployment in the corresponding fields.

The advantage is a maximum utilization of the availability and statistical data for the training, since a large selection of diverse imaging devices can be used in different facilities for training, without sensitive data having to leave the respective protected networks. In this respect in particular rare pathologies or pathologies in the case of ethnic minorities can be more effectively identified, in particular if special settings would have to be made on the devices in this respect.

In the case of a combination or mixture of two AIs it should be noted that not simply mean values of the parameter datasets can be formed. In this case AIs should always be used that although they have been trained at different locations have however all been trained for the same specific application, in other words solve the same task in principle, even if the objects of the image recordings should be different. In principle all AIs present in the central computing apparatus have been trained, but have not necessarily been trained equally well for all body regions. As stated above, an AI from a head clinic may be trained extremely well for head recordings and only very poorly for thorax recordings. In a lung clinic the reverse is generally the case. The AIs collected by the central computing apparatus can thus in principle solve the same tasks (e.g. identify pathologies or optimize a positioning or a collimation) but possibly for recordings on different organs.

A mixture or combination preferably predefines the weighting for how a trained AI supplies its contribution for which specific application and could in practice take place as follows:

A selection of trained AIs could be made available that provide a number of organ applications for a number of patient classes. The best AI is in each case selected for each of the possible applications.

A meta-algorithm (a normal or machine learning algorithm) could be created which combines the AIs. Preferably this is a neural meta-network that is trained based upon data available in the central server. The trained network decides which AI contributes, with which weighting, for which application (e.g. head, foot, heart) for which patient (e.g. child, adult, fat, thin, short, tall).

Instead of using a neural network at the meta-level another algorithm, e.g. a genetic algorithm, could be formed which selects which AI contributes for which applications at which weighting factor on average.

One advantage of at least one embodiment of the invention is that an AI can be trained without confidential private data having to be passed to a central hub of an AI provider. This is because the data of the neural network, which can be passed to a hub for further development, validation and release, does not enable the input data relevant to data protection to be retraced. The AI can even be continuously or iteratively trained technically and as a result slowly improved. If the AI is trained by the operator directly vis-à-vis the image recording and not vis-à-vis the visual perception of the patient, the algorithm improves iteratively, in order to generate precisely the ideal image quality and collimation as is desired in the final cropped and tuned image. This can have enormous advantages for the image quality and dose. Cropping (manually or automatically) is no longer required, as a result of which time-consuming work procedures can be obviated and the waste of an applied dose reduced. Furthermore, for each given AI-controlled prediction of scanning parameters based on sensor data the AI algorithm can improve itself over time for a particular patient population at a particular hospital site, if the use of the device increases, without updates having to be received from the central location. Wider applications of organ identification (e.g. shoulder in addition to thorax) are possible as soon as sufficient recordings of the organ have been performed locally, based on which it is possible to learn.

In the following explanations it is assumed that the imaging system is a CT system. The method can however in principle also be deployed on other imaging systems from within the medical engineering field and outside it.

FIG. 1 shows roughly schematically a computed tomography system 1 with a control facility 5 for performing an embodiment of the inventive method. The computed tomography system 1 has, as is customary, a scanner 2 with a gantry, in which an X-ray source 3 rotates, which in each case transirradiates a patient P, who is pushed into a measurement area of the gantry via a couch, such that the radiation hits a detector 4 in each case opposite to the X-ray source 3. It is explicitly noted that this example embodiment is only an example of a CT and the invention can also be used on any CT constructions, for example with an annular stationary X-ray detector and/or multiple X-ray sources.

Likewise for the control facility 5 the only components shown are the ones that are important for the explanation of the invention. These types of CT systems and associated control facilities are known in principle to the person skilled in the art and hence do not need to be explained in detail.

A core component of the control facility 5 here is a processor 11, on which different components are implemented in the form of software modules. The control facility 5 furthermore has a terminal interface 14, to which a terminal 7 is connected, via which an operator can operate the control facility 5 and thus the computed tomography system 1 or can appraise image recordings B. A further interface 15 is a network interface for connection to a data bus 21, in order in this way to establish a connection to an RIS (Radiology Information System) or PACS (Picture Archiving and Communication System).

The scanner 2 can be controlled by the control facility 5 via a control interface 13, i.e. for example the rotation speed of the gantry, the movement of the patient couch and the X-ray source 3 itself are controlled. The raw data RD is read out from the detector 4 via an acquisition interface 12.

Furthermore, the control facility 5 has a storage unit 16, in which various measurement protocols are stored, among other things.

A further component on the processor 11 is an image data reconstruction unit 18, with which the desired image data is reconstructed from the raw data RD received via the data acquisition interface 12.

Image recordings B can be appraised by a user via the terminal 7 and a ground truth G can also be assigned to these, e.g. whether a pathology is present or whether or not an image is good. This has happened in the case shown here and the image recordings B can be stored in the storage unit 16 together with the relevant ground truth G for each image as a training dataset T. The image recordings B need not in this case necessarily be part of the training datasets and are hence shown in the storage facility 16 besides the training datasets T. The ground truth G can be supplemented by data from a sensor 22, e.g. a 3D camera 22.

In this example the training unit additionally comprises a verification algorithm U, which is designed to verify parts of the training datasets T or image recordings B and e.g. to reorient them or to decide upon them. The changes made by the verification algorithm U are incorporated into the respective ground truths G.

The training unit 6 need not necessarily be located in the control facility 5, but can also be present in a separate computer, and receive the training datasets T via the data bus 21, as indicated by dashed lines.

The parameter dataset PD of the trained algorithm A is sent, e.g. via the data bus 21, via the data interface 19 to a network 17 outside the hospital network 9 (here and in the following figures, a hospital network 9, 10 represents a secure data connection 9). Located there is a central computing apparatus 20, which receives the parameter dataset PD and creates a trained machine learning algorithm A therefrom. In the example shown here the central computing facility 20 has already received a trained machine learning algorithm A1 from another hospital network 10. These two machine learning algorithms A, A1 can now be combined with one another.

As a whole FIG. 1 sketches a multi-device network 8 in accordance with a preferred embodiment of the invention.

Figure 2:
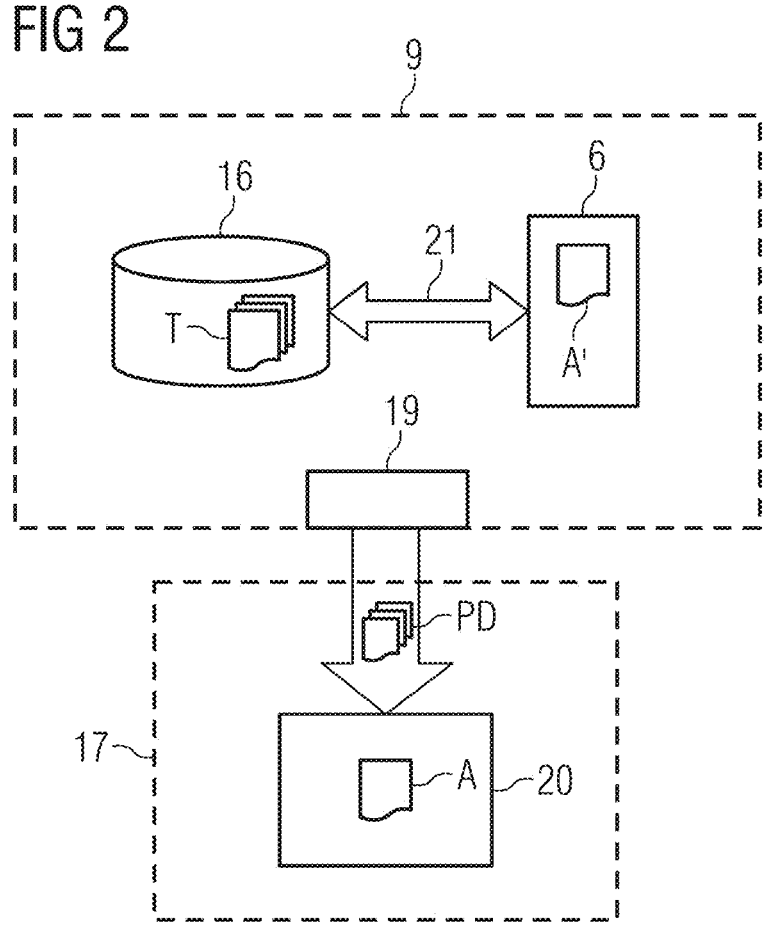
FIG. 2 is an embodiment of an inventive system.

FIG. 2 shows an embodiment of an inventive system for training a machine learning algorithm. This illustration resembles FIG. 1 in principle, but provides a better overview of the major core components. The system comprises the following components:

a training apparatus 6 with a machine learning algorithm A' to be trained within a secure hospital network 9, a central computing apparatus 20 designed to operate a trained machine learning algorithm A in a network 17 outside the hospital network 9, a data interface 19 designed to send data from the training apparatus 6 to the central computing apparatus 20, a storage facility 16 for a plurality of training datasets T based on image recordings, a communication unit 21 (which could e.g. be the data bus 21 from FIG. 1) designed to send training datasets T within the hospital network 9 to the training apparatus 6.

Figure 3:
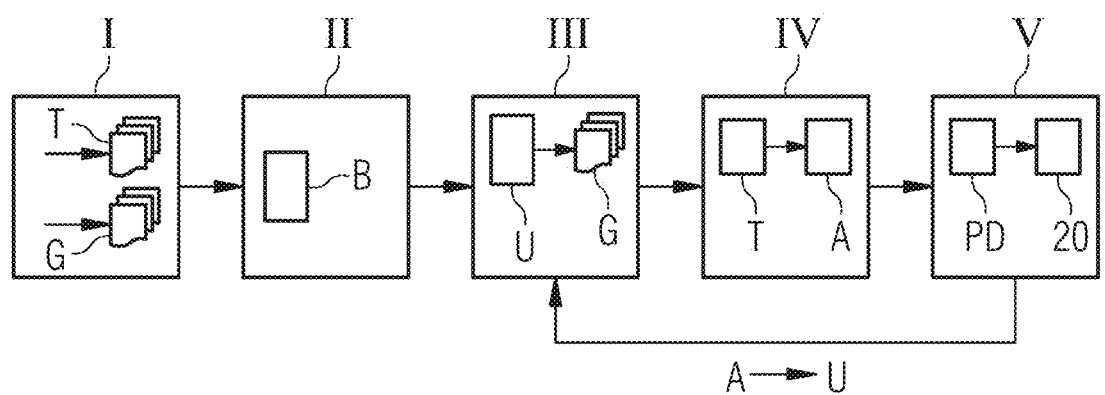
FIG. 3 is a flowchart for a possible sequence of an embodiment of an inventive method.

FIG. 3 shows a flowchart for a possible sequence of an embodiment of an inventive method for training a machine learning algorithm A.

For a better overview it is assumed to this end that all components, as e.g. shown in FIGS. 1 and 2, are available.

Step I entails a presetting for the acquisition of images. This comprises e.g. the positioning of a patient P by an MTRA, a setting of the recording parameters, a measurement of the patient P via sensors 22 and/or a prediction of a (partially trained) AI using ideal system parameters for the corresponding examination, wherein the presetting of the imaging system 1 could certainly be effected by the AI. All these presettings are preferably stored in the training datasets (they are all based on the acquisition of images to be performed).

A user can correct predictions or presettings of the AI. These predictions are then preferably incorporated into the ground truth G.

In step II an image recording B is created with an imaging system 1, e.g. a CT system 1 from FIG. 1.

In step III a verification algorithm U (e.g. a further previously trained AI) analyzes the image recording B created and evaluates whether settings were "good" or "bad" or if appropriate calculates what better presettings would have been. If the image recording B needs to be cropped, the original collimation was too large. If the image recording B is too noisy, the dose should have been higher. If the joint space is not visible, the angle of the tube geometry should have been different. All these findings are incorporated into the ground truth G.

Alternatively or additionally a user (e.g. an MTRA at the scanner or a radiologist at the diagnostic monitor) can evaluate the image recording accordingly (independently of the verification algorithm U or the results of the verification algorithm U). It can happen in this case that corrections are only possible during cropping or rotating. If the dose was too low, a comment is made e.g. in the ground truth; if the geometric recording parameters were wrong (joint space or wrong recording region) the image recording B can also be rejected.

The following cases now therefore exist, namely that the image recording B was correct (this is noted in the ground truth G), the image recording B has been changed (the changes are noted in the ground truth G), the image recording B was rejected (the corresponding training dataset T is rejected or the rejection is noted in the ground truth G).

In step IV the machine learning algorithm A is trained.

In step V the parameter value dataset PD of the trained machine learning algorithm A is sent to the central computing apparatus 20 outside the hospital network 9.

The AI trained in this way can now be used as a monitoring algorithm U or as an algorithm for predicting the presettings.

However, thanks to its basic structure, an embodiment of the inventive method provides the opportunity of combining the findings from multiple independent facilities with one another, without sensitive data having to be disclosed.

The trained AIs received from multiple independent facilities can now be compared with one another or combined with one another on the central computing apparatus 20. For example, the most powerful AI is authorized as a medical product and is sent back to all imaging devices in order to be used there, and e.g. to make more accurate predictions about kV, mAs, collimation, degrees of geometric system freedom.

However, the best AI also does not necessarily need to be selected, but by way of smart "mixing" or "combination" or "interconnection" of the various trained AIs an even more powerful AI can be created, which in turn is better than all previous AIs. This mixed AI can then be deployed on the individual devices.

Figure 4:
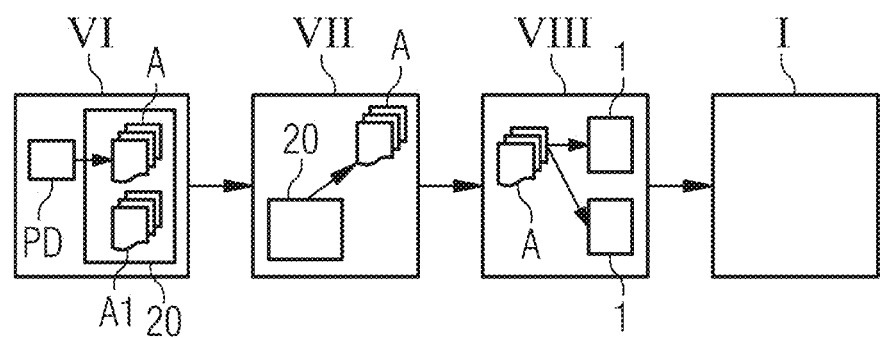
FIG. 4 is a flowchart for a possible further sequence of an embodiment of the method according to FIG. 3.

FIG. 4 shows a flowchart for a possible further sequence of an embodiment of the method according to FIG. 3.

In step VI further trained machine learning algorithms A1 are sent to the central computing apparatus 20 in the form of parameter datasets PD. The central computing apparatus 20 then contains multiple trained machine learning algorithms A, A1.

In step VII a selection is made of the best machine learning algorithm A, A1 and/or a combination of the machine learning algorithms A, A1. In this example the algorithm A is selected as the more powerful one.

In step VIII the selected machine learning algorithm A is sent to imaging systems 1, which can certainly take place via the corresponding parameter dataset PD.

The training can thereafter be continued, wherein the machine learning algorithm A is further trained, which is indicated with a following box bearing the number I.

In conclusion it is noted once again that the method described in detail above and the systems illustrated are merely example embodiments which can be modified in a wide variety of ways by the person skilled in the art, without departing from the scope of the invention. Furthermore, the use of the indefinite article "a" or "an" does not exclude the possibility of the features in question also being present multiple times. Likewise the terms "unit" and "module" do not exclude the possibility that the components in question includes multiple interacting subcomponents which if appropriate can also be distributed spatially.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for training a machine learning algorithm, the method comprising:
   provisioning a training apparatus with a machine learning algorithm to be trained, the training apparatus having a secure data connection to a medical-engineering imaging system;
   creating a plurality of training datasets based on image recordings, each training dataset of the plurality of training datasets being furnished with a ground truth or being linked by a data link;
   sending training datasets, of the plurality of training datasets, to the training apparatus via the secure data connection;
   training, via the training apparatus, the machine learning algorithm with the training datasets to create a trained machine learning algorithm and to specify parameters for a radiological examination on a patient-specific basis; and
   sending a parameter dataset of the trained machine learning algorithm to a central computing apparatus.

2. The method of claim 1, wherein before the training datasets are sent to the training apparatus, the method further comprises:
   analyzing a quality of the image recordings based upon criteria; and
   rejecting or adjusting a respective image recording of the image recordings upon the quality not satisfying the criteria for the respective image recording, wherein the adjusting adjusts the respective image recording to correspond to the criteria or is rejected.

3. The method of claim 2, wherein the method further comprises:
   including the respective image recording in a respective ground truth upon the adjusting of the respective image recording.

4. The method of claim 3, wherein the method further comprises:
   rejecting a corresponding training dataset or characterizing the corresponding training dataset as a negative example upon the respective image recording not being adjustable.

5. The method of claim 2, wherein the ground truth assigned to an image recording comprises information at least one of about settings made for recording the respective image recording or changes made to the image recording, and the method further comprises:
   automatically recording the information when making the respective settings.

6. The method of claim 2, wherein the method further comprises:
   performing an analysis of the image recordings based upon criteria via a previously trained verification algorithm configured to evaluate a quality of a respective image recording based upon the criteria, wherein the performing the analysis is performed independent of or in addition to an analysis by a user.

7. The method of claim 6, wherein, upon the respective image recording not satisfying the criteria, the method further comprises:
   adjusting the respective image recording to correspond to the criteria, or determining which recording parameters to change during a recording, and how to change the recording parameters so that the respective image recording satisfies the criteria.

8. The method of claim 7, wherein the method further includes:
determining, based upon the adjusted respective image recording, how positioning of a patient should have taken place, during an original image recording, to satisfy the criteria.

9. The method of claim 1, wherein
the ground truth assigned to an image recording includes information about settings made for recording the respective image recording or changes made to the image recording, and
the information is recorded automatically when making the respective settings.

10. The method of claim 1, wherein
the machine learning algorithm is a CAD algorithm, and
the ground truth for an image recording includes a diagnosis and information on postprocessing of the image recording.

11. The method of claim 10, wherein information on postprocessing of the image recording includes information on changes in at least one of contrast, brightness, highlightings of structures, or changes in positions of picture elements.

12. The method of claim 1, wherein
sensor data from a corresponding medical-engineering imaging system is recorded during the creating of the plurality of training datasets, and
the sensor data includes image data.

13. The method of claim 12, wherein the sensor data includes image data from at least one of a 3D camera, an ultrasound detector, or a radar detector.

14. The method of claim 1, wherein at least two trained machine learning algorithms or parameter datasets are used in the central computing apparatus for at least one of mutual evaluation or validation.

15. The method of claim 14, wherein the at least two trained machine learning algorithms are trained on the same organs.

16. The method of claim 15, wherein a number of the machine learning algorithms are trained within different training apparatuses.

17. The method of claim 15, wherein the method further comprises:
making available, by the central computing apparatus, a best evaluated or validated machine learning algorithm for use by medical facilities.

18. The method of claim 1, wherein at least two trained machine learning algorithms or parameter datasets are at least one of combined or mixed with one another in the central computing apparatus.

19. The method of claim 1, further comprising:
storing the trained machine learning algorithm on a non-transitory computer readable medium.

20. The method of claim 1, wherein the parameters include degrees of freedom of at least one of modality or position of a patient.

21. The method of claim 20, wherein the parameters include at least one of collimation, dimensioning of spatial axes, orientation of a coordinate system, tube voltage, X-ray current, intensity of an X-ray beam, position of the patient or of a patient couch, orientation of the patient or of the patient couch, position of a recording window, or recording time.

22. The method of claim 1, further comprising:
provisioning the central computing apparatus, the central computing apparatus being designed to operate a trained machine learning algorithm in a network without direct access to the secure data connection; and
provisioning a data interface, the data interface being designed to send data from the training apparatus to the central computing apparatus.

23. A controller for controlling an imaging system, the controller configured to train a machine learning algorithm by at least:
provisioning a training apparatus with a machine learning algorithm to be trained, the training apparatus having a secure data connection to a medical-engineering imaging system;
creating a plurality of training datasets based on image recordings, each training dataset of the plurality of training datasets being furnished with a ground truth or being linked by data link;
sending training datasets, of the plurality of training datasets, to the training apparatus via the secure data connection;
training, via the training apparatus, the machine learning algorithm with the training datasets to create a trained machine learning algorithm and to specify parameters for a radiological examination on a patient-specific basis; and
sending a parameter dataset of the trained machine learning algorithm to a central computing apparatus via a data interface.

24. An imaging system comprising:
a scanner; and
a controller configured to control the scanner and train a machine learning algorithm by
provisioning a training apparatus with a machine learning algorithm to be trained, the training apparatus having a secure data connection to a medical-engineering imaging system,
creating a plurality of training datasets based on image recordings, each training dataset of the plurality of training datasets being furnished with a ground truth or being linked by data link,
sending training datasets, of the plurality of training datasets, to the training apparatus via the secure data connection,
training, via the training apparatus, the machine learning algorithm with the training datasets to create a trained machine learning algorithm and to specify parameters for a radiological examination on a patient-specific basis, and
sending a parameter dataset of the trained machine learning algorithm to a central computing apparatus via a data interface.

25. A multi-device network comprising:
a plurality of training apparatuses with secure data connections to different imaging systems;
a central computing apparatus designed to operate a trained machine learning algorithm in a network, the trained machine learning algorithm being trained by
provisioning a training apparatus with a machine learning algorithm to be trained, the training apparatus having a secure data connection to a medical-engineering imaging system;
creating a plurality of training datasets based on image recordings, each training dataset of the plurality of training datasets being furnished with a ground truth or being linked by a data link;

sending training datasets, of the plurality of training datasets, to the training apparatus via the secure data connection;

training, via the training apparatus, the machine learning algorithm with the training datasets to create the trained machine learning algorithm and to specify parameters for a radiological examination on a patient-specific basis; and sending a parameter dataset of the trained machine learning algorithm to the central computing apparatus; and data interfaces designed for data communication between the plurality of training apparatuses and the central computing apparatus, wherein the network does not include direct access to secure data and the multi-device network is configured to enable parameter datasets to be sent between the plurality of training apparatuses and the central computing apparatus.

26. The multi-device network of claim 25, wherein the central computing apparatus is configured to combine at least one of parameter datasets or machine learning algorithms with one another.

27. A non-transitory computer-readable medium, storing program sections, readable and executable by a computer unit, to execute a method when the program sections are executed by the computer unit, the method comprising:

provisioning a training apparatus with a machine learning algorithm to be trained, the training apparatus having a secure data connection to a medical-engineering imaging system;

creating a plurality of training datasets based on image recordings, each training dataset of the plurality of training datasets being furnished with a ground truth or being linked by a data link;

sending training datasets, of the plurality of training datasets, to the training apparatus via the secure data connection;

training, via the training apparatus, the machine learning algorithm with the training datasets to create a trained machine learning algorithm and to specify parameters for a radiological examination on a patient-specific basis; and sending a parameter dataset of the trained machine learning algorithm to a central computing apparatus.

* * * * *